United States Patent [19]

Maurer et al.

[11] 4,155,827

[45] May 22, 1979

[54] ELECTRO-CHEMICAL SENSOR CONSTRUCTION

[75] Inventors: Helmut Maurer, Schwieberdingen; Franz Rieger, Aalen-Wasseralfingen; Ernst Linder, Muhlacker, all of Fed. Rep. of Germany

[73] Assignee: Robert Bosch GmbH, Stuttgart, Fed. Rep. of Germany

[21] Appl. No.: 918,145

[22] Filed: Jun. 22, 1978

[30] Foreign Application Priority Data

Jun. 30, 1977 [DE] Fed. Rep. of Germany ....... 2729475

[51] Int. Cl.$^2$ ............................................ G01N 27/58
[52] U.S. Cl. ................................................. 204/195 S
[58] Field of Search ............. 204/195 S, 1 S; 60/276; 123/119 E; 324/29, 71 R

[56] References Cited

U.S. PATENT DOCUMENTS

| 3,546,086 | 12/1970 | Sayles .............................. 204/195 S |
| 3,871,981 | 3/1975 | Flais et al. ....................... 204/195 S |
| 3,960,692 | 6/1976 | Weyl et al. ...................... 204/195 S |
| 4,021,326 | 5/1977 | Pollner et al. .................. 204/195 S |

FOREIGN PATENT DOCUMENTS 2307451 8/1974 Fed. Rep. of Germany ....... 204/195 S

*Primary Examiner*—G. L. Kaplan
*Attorney, Agent, or Firm*—Flynn & Frishauf

[57] ABSTRACT

An electro-chemical sensor to determine the oxygen content of exhaust gases, particularly from internal combustion engines. The sensor contains a tubular solid electrolyte closed at one end having a catalytically active layer on the outside to be exposed to the exhaust gas. The inside of said solid electrolyte tube is exposed to the ambient air and is provided with a contact portion arranged at the bottom of said solid electrolyte tube. The sensor contains an elongated axial center electrode which is pressured against the bottom (closed end) of the inside of the tubular solid electrolyte, preferably by means of a compression spring which may be mounted internal of said center electrode or external thereof. The central electrode comprises an insulating body having a heating element in the area which will be adjacent the portion of the solid electrolyte in contact with the exhaust gases. Additionally the central electrode also carries an electric lead to said contact portion. The contact portion may be attached to the central electrode.

13 Claims, 5 Drawing Figures

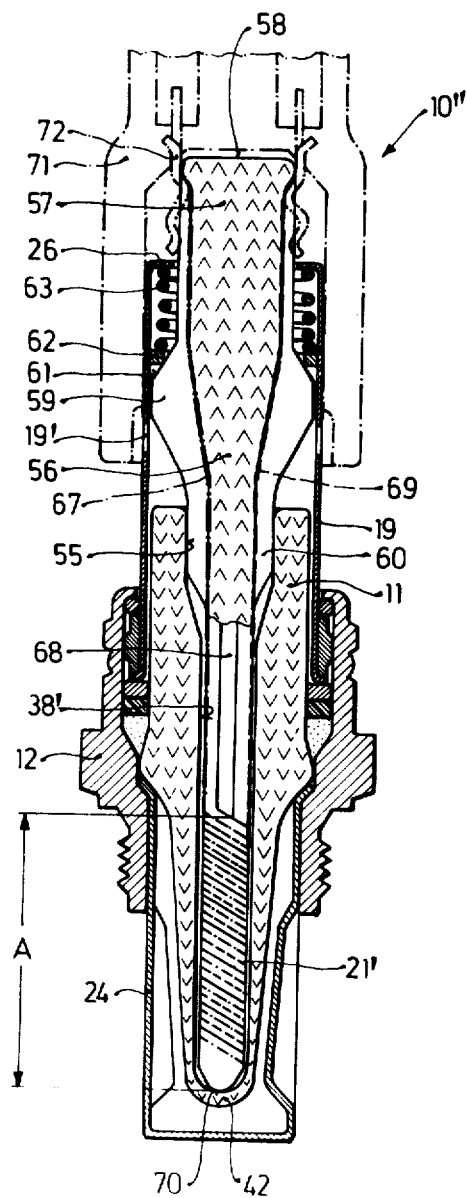
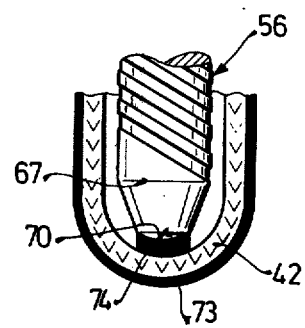
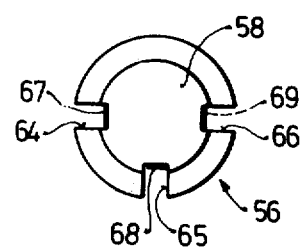

ELECTRO-CHEMICAL SENSOR CONSTRUCTION

BACKGROUND OF THE INVENTION

The present invention provides an oxygen sensor adapted to contact exhaust gases, particularly of internal combustion engines which are ultimately used as part of the control of the fuel-air ratio, thereby controlling the emission content of the exhaust gas. The sensor of the present invention has an improved construction, including a heating element.

The basic prior art sensor of which the present invention is an improvement is of the type disclosed in German disclosure document OS 2 307 451. The sensor disclosed in the German publication does not include a heater element.

U.S. Pat. No. 3,546,086 discloses an electrochemical sensor which includes a heater element in the inner space of the closed end tubular solid electrolyte. The sensor disclosed in this patent has the design disadvantage that the inner electrode or the electrical contact to said electrode located in the inner space of the solid electrolyte requires an expensive coating on the interior surface of the tubular solid electrolyte.

It is an object of the present invention to provide an improved oxygen sensor containing a heater element which is economic in terms of materials and in terms of construction leading to an improved product.

THE INVENTION

An electro-chemical sensor to determine oxygen having a closed-ended substantially tubular solid electrolyte with an inner contact portion and an outer catalyst in ion communication through the solid electrolyte. The inner contact portion and the outer catalyst are in electrical connection through an external measurement circuit. The sensor also includes an inner elongated insulator within the tubular solid electrolyte in resilient contact with the inside portion of the closed end of the solid electrolyte. The elongated body carries an electrical lead which is in contact with the inner contact portion and with the measurement circuit. The elongated body also includes a heater element in the section of said elongated body adjacent the portion of the solid electrolyte adapted to contact the exhaust gases. The outer catalyst may be connected to the measurement circuit through the chassis, or by a separate electrical lead. The sensor includes means for bringing a portion of reference air into the interior thereof to the inner contact portion.

The elongated inner electrode is pressed against the inner closed end of the tubular solid electrolyte, preferably by a compression spring which may be mounted internal of said inner electrode assembly as illustrated in FIGS. 1 and 2, or external thereof as illustrated in FIG. 3.

The inner electrode carries the electric contact to the inner contact portion The inner contact portion may be a layer formed on the inner surface of the closed-end portion of the solid electrolyte (or closely adjacent thereto), or may be a plate or coating on the end of the elongated inner electrode which is pressed in contact with the inner closed end of the tubular solid electrolyte.

The inner elongated electrode includes an insulator body having a heater element in the portion thereof which is adjacent the portion of the tubular solid electrolyte adapted to contact the exhaust gas. This permits heating the solid electrolyte which functions to quickly bring the sensor to the minimum temperature at which it operates when starting a cold engine. This is particularly important if the sensor is located relatively far from the engine. The heating of the sensor also renders it more resistant to the deleterious influence of poisons, mainly lead, present in the fuel or engine emissions.

The heater element is preferably in the form of a double wound arrangement of the heating element around (or adjacent) the outer surface of the insulator. This provides a spiral winding arrangement. The two leads to the heater may both be continued all the way to the contact end of the sensor, or they may terminate at intermediate portions of the peripheral surface thereof in suitable contact arrangement, such as those disclosed in the drawings. In the spiral winding arrangement, it is preferred that the contact lead carried by the center electrode to the inner contact portion should also be in parallel with the heater winder elements.

The invention will be described by way of example with reference to the accompanying drawings wherein:

FIG. 3 is a similar longitudinal sectional view of a sensor having an inner body including an insulating body which carries conductive strips and is also shaped to form the connector body;

FIG. 4 is a top view of the insulating body of the inner body of FIG. 3; and

FIG. 5 is an enlarged detail of the exhaust gas end of the sensor of FIG. 3.

Figure 1:
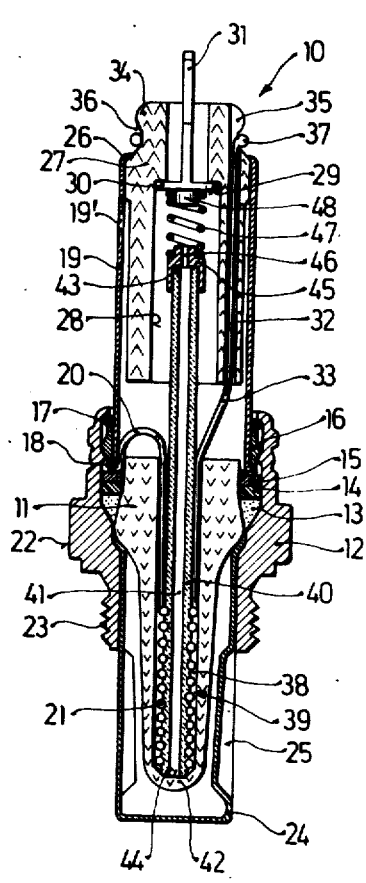
FIG. 1 is a longitudinal sectional view in an enlarged scale through a gas sensor having a single terminal connection to the heating element.

Referring to FIG. 1, electrochemical sensor 10 contains a tubular solid electrolyte 11 having a closed end 42. The outer surface of solid electrolyte tube 11 is adapted to be exposed to the exhaust gases from an internal combustion engine. It is coated with a catalytically active electrically conductive layer, such as layer 73 in FIG. 5. The other end section of the tubular solid electrolyte 11 (in the direction of the contact end) is surrounded by a metallic housing 12 and is fixed in this housing by the combination of the contact packing 13, the insulating washer 14, the metallic spacer 15, the guide bushing 16, and the thrust collar 17. The lower flange 18 of the upper protective housing 19 and the ground (chassis) connection 20 of the heating element 21 are positioned between the spacer 15 and the guide bushing 16.

The upper protective housing 19 contains a number of openings 19' which permit the surrounding air to enter the sensor 10. The sensor housing 12 is formed with an outside in the shape of a hexagon 22 to fit a hexagonal wrench and also shaped with externally threaded bushing 23 for insertion into an exhaust pipe from an internal combustion engine. Protective tubular member 24 which is spaced apart from and surrounds the closed end portion of the tubular solid electrolyte 11 adapted to be exposed to the exhaust gases, descends from and is fixed to the housing 12. Slots 25 in the protective housing 24 permit a controlled flow of the exhaust gas to reach the solid electrolyte 11 coated by the catalytically active layer.

At the other end of the housing 12 (the contact end), upper protective housing 19 forms a tubular extension having an inwardly rolled rim (crimped) 26 positioning an insulator body 27 which extends in both directions, that is beyond the protective housing 19 in the direction in which the sensor 10 is connected and also inside the protective housing 19. Insulator body 27 is provided with a recessed axial bore hole 28 in the lower portion forming an upper shoulder 29. This shoulder 29 of the insulator body 27 abuts the flange 30 of the blade terminal 31 which forms a stem protruding upwardly through and out of the insulator body 27 and functions as the positive terminal of the sensor 10. Another axially extending hole 32 extends lengthwise through the insulator body 27 and provides a channel in which is located the positive terminal 33 of the heating element 21.

The connector end of the insulator body 27 extends in the shape of a slightly mushroomed (extended) configuration 34 which includes a detent 35 for a connector body (socket) and includes a neck section carrying a contact ring 37 connected to the positive connection 33 of the heating element 21.

The tubular solid electrolyte 11 has an inner space 38 in which is positioned the center electrode 39, the lower end 44 of which is positioned solidly on the contact portion 74 on the bottom 42 of the tubular solid electrolyte 11. The center electrode 39 comprises a tubular electroinsulating body 40 and an electric conductor 41. The electric conductor 41 is a conductive strip which runs through the entire bore of the electro-insulator 40 and extends over the lower end face 44 and the upper end face 43 of the electric insulator 40. It is possible to replace said electric insulator body 40 with a solid rod electric insulating body which is shaped to fit within the space 38 and contains an axial channel for an electric conductor corresponding to conductor 41 (the rod insulator body 40 is not illustrated). Another alternate embodiment which is not illustrated uses a tubular electroinsulator body 40 having a tubular electric conductor 41 positioned in the central bore of the tubular insulator body 40.

An area on the inner surface of the bottom 42 of the solid electrolyte is covered with a said contact portion 74, for example a porous platinum layer having a large degree of porosity. The area of said contact portion at least covers that area in contact with the lower end face 44 of the electric conductor 41 of the central electrode 39 as illustrated in FIG. 5.

The end face 43 of the central electrode 39 at the contact end of the sensor 10 is enclosed with a metal nipple 45 having a central hole 46. A (pre-loaded) compression spring 47 is positioned on top of and against said nipple 45; the other side of said spring 47 presses against the flange 30 of the terminal contact. A boss on said flange 30 functions to align said spring 47.

The electric insulator 40 of the central electrode 39 contains a heating element 21 located on its outer surface in the end of the sensor which is adapted to be exposed to the exhaust gases. The heating element 21 consists of a double wound resistance wire. The resistance wire is positioned in spiral grooves (not provided with position number) in the outer surface of the insulator 40. Said spiral grooves end just above the contact area formed between the electric conductor 41 and the bottom 42 of the tubular solid electrolyte 11. The heating element 21 is manufactured integrally with its positive connection 33 and the chassis connection 20. As a result the center electrode 39 and the heating element 21 form a readily assembled compact unit which is readily adapted to be mass produced.

The tubular solid electrolyte 11 is an ion conductive material, preferably including or totally made of a cubic stabilized zirconium dioxide. In addition to the catalytic electron conductive coating 74 on the outer surface which is adapted to contact the exhaust gases, other coatings may be provided over all or various portions of the tubular solid electrolyte 11 as is well known, for example as disclosed in U.S. Pat. No. 4,021,326. The outer catalytic layer 73 is electrically connected through the electric measurement circuitry to the inner contact portion 74 via, inter alia, conductor 41.

Figure 2:
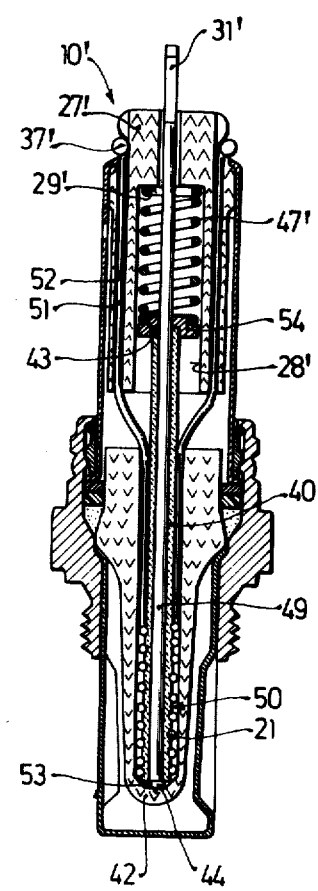
FIG. 2 is a similar longitudinal sectional view of a sensor having two terminal connections to the heating element.

The electrochemical sensor (oxygen sensor) 10' illustrated in FIG. 2 is similar to the sensor illustrated in FIG. 1; however it is distinguished by having the electric conductor 49 of the inner electrode body 50 extending from the bottom 42 of the tubular solid electrolyte 11 directly to the blade terminal 31', and by having the chassis lead contact 51 located in a second longitudinal bore hole 52 through the insulator body 27' extending upward to a terminal 37'.

The electric conductor 49 is a rod having a uniform cross section running the entire length of the sensor 10'. Its head portion 53 contains as contact portion a flat end plate of a noble metal, such as silver, and it is located so that it contacts the bottom 42 of the tubular solid electrolyte 11. The tubular electric insulator 42 surrounds the rod electric conductor 49 and rests with its annular lower end 44 on the head 53 which extends from the electric conductor. The other annular end 43 of the insulator 40 is positioned and located within a ring shaped thrust collar 54 which is preferably made of a ceramic and forms the seat 44 of a preloaded compression spring 47'. The other end of the spring 47' abuts the shoulder 29' which is recessed in the large center bore hole 28' in the insulating body 27'.

The electric conductor 49 which is centrally located in the center electrode is positioned axially and centrally throughout the tubular portion of the sensor 10 and provides a functionally positive and dependable guide for the connection of the positive terminal 10'. In this embodiment of the sensor 10', the heating element 21 is similarly wound around the outer surface of the insulator body 40 in the double wound arrangement.

FIG. 3 illustrates a sensor 10" which has a particularly uncluttered mechanical design, is economic, and is particularly adaptable to be mass produced. The construction and design arrangement of the housing 12, the tubular solid electrolyte 11, the upper protective housing 19, the lower outer protective housing 24, and the packing components for the tubular solid electrolyte 11 in the housing 12 generally correspond to the corresponding details of the sensor 10' illustrated in FIG. 2. The inner space 38' of the tubular solid electrolyte 11 is outwardly flared in the direction of the contact end of the sensor, resulting in an enlarge inner space 55 at the upper portion of the inner space 38'. An insulator body 56 extends downwardly from the connector end into the inner space 38'. The inner extended end of the insulator body 56 rests on the inside of the bottom 42 of the tubular solid electrolyte 11. The other end of the insulator 46 (at the contact end) is enlarged to form an expanded head section 57. The insulator body 46 also includes a circumferencial flange 59 between its end sections. The upper end of the flange 59 does not extend all the way to the end plane 58 of the head section 57 of the insulator 56. The outer diameter of the flange 59 is somewhat smaller than the inner diameter of the protective housing 19, thereby permitting the flange 59 to act as a guide for the insulator body 56. In the direction of the closed end of the tubular sensor, the flange 59 contracts to form a guide portion 60 which fits into the enlarged inner space 55 of the tubular solid electrolyte 11. A thrust collar 62 is positioned on the shoulder 61 in the direction of the contact end of the flange 59. The thrust collar 62 supports one end of a preloaded extension spring 63, the other end of which is constrained by the inwardly directed upper rim 26 of the protective housing 19. As a consequence, the pressure exerted by the compression spring 63 is transmitted to the insulating body 56 as a whole.

That portion of the insulator body 56 comprising the head portion 57 and the flange 59 together with the lower extended guide portion of the flange 60 contains three longitudinal channels (grooves) 64, 65, and 66. Channel 64 functions to accept (contain) a conductive strip 67 which is connected to the positive terminal of the sensor 10". Channel 65 contains a conductive strip 68 which is the positive contact to the heating element 21'. Channel 66 contains the conductive strip 69 which is the negative contact to the heating element 21'. Within the above-described portion of the insulator 56, and the associated flange 59, and guide 60, the three conductive strips or wires 67, 68, and 69 are positioned in the axial direction of the sensor 10". They extend beyond the guide portion 60 of the central insulator 57 to the portion indicated by the letter A of the insulator 56 which adjoins that portion of the tubular solid electrolyte 11 adapted to be exposed to the exhaust gases.

Each of the conductive strips (67, 68, and 69), within that portion of the electrode designated by the letter A, is spirally wound in a plurality of turns so that there is no contact between the respective strip 67, 68, and 69 and they are in parallel paths (or tracks). The two conductive strips (68, 69) which are the contacts for the heating element 21' do not extend all the way to end plane 70 of the insulator 56. Their terminals are electrically connected with each other so that together they form the heating element 21' in the section of the insulator 56 near, but spaced away from, the closed end section 42 of the tubular solid electrolyte 11. The conductive strip 67 overlays the end plane of the insulator body 70, thereby seating itself on the bottom 42 of the tubular solid electrolyte 11, illustrated in the FIG. 5 detail view; in this preferred embodiment between the conductive strip 67 and the end plane of the insulator body 70 is arranged a contact portion 74, usually consisting of a noble metal als platinum.

The conductive strips 68, 69 in the sensor 10" are positioned in a double wound arrangement. A mixture of palladium and glass can be used to form the conductive strips 67, 68, and 69. The positioning of the three conductive strips 67, 68, and 69 in parallel with each other in the area designated A can be produced by first completely coating the surface area of the insulator 56 in the axial portion designated by the letter A with a palladium-glass mixture and, after firing, removing by grinding portions of the palladium-glass mixture to form parallel channels which are insulators leaving the remaining palladium-glass in the form of three parallel spiral conductive strips, 67, 68, and 69. The terminals of the conductive strips 67, 68 and 69 at the enlarged top section 57 of the insulator are used as the terminals to establish contact with the sensor 10". A contact socket 71 with spring contacts 72 molded therein is illustrated with dashed lines in FIG. 3.

The air entering through the orifices (slots) 19' in the protective housing 19 can flow to the point wherein the conductive strip 67 is in contact with the bottom 42 and the contact portion applied thereto on the tubular solid electrolyte. The air flows through the portions of the channels 64, 65, and 67 in the area of the guide section 60 and further through a narrow groove which is left between the insulator 56 and the tubular solid electrolyte 11. The grinding operation may be controlled so that the electric resistance of the heating element 21' can be regulated by the grinding operation.

Various changes in modifications may be made within the scope of the inventive concept.

We claim:

1. An electrochemical sensor for the determination of oxygen content of gases particularly the exhaust gases of internal combustion engines comprising
    a housing,
    a closed end substantially tubular solid electrolyte secured in said housing with the closed end adapted to be exposed to exhaust gas, said solid electrolyte having an outer catalytic layer in the portion thereof adapted to be exposed to the exhaust gas and a contact portion in ion contact with the inside so that the solid electrolyte provides ion communication between the catalytic layer and said contact portion, said catalytic layer and said contact portion being electrically connected through an external measurement circuit
    and comprising in accordance with the invention,
    an inner elongated insulator body in resilient contact with the inside portion of the closed end of said tubular solid electrolyte, said elongated body carrying an electric lead which is in contact with said inner contact portion and also in electric contact with said measurement circuit, and said elongated body also comprising electric resistance heater element means in the portion of said elongated body adjacent the portion of said tubular solid electrolyte adapted to be exposed to the exhaust gases, said heater element means having contact for leads on or through said elongated insulator body for connection to a power circuit supplying the electricity to cause said resistance heater element to heat.

2. The sensor of claim 1 wherein said inner elongated insulator body is pressed into resilient contact with the inside portion of the closed end of said tubular solid electrolyte by means of a compression spring positioned in contact with the other end portion of said elongated body, said compression spring being secured within the housing of the sensor.

3. The sensor of claim 2 wherein said spring is positioned between said inner elongated body and the end of said sensor which is not adapted to be exposed to the exhaust gas.

4. The sensor of claim 2 wherein said inner elongated body is positioned centrally of said sensor with the compression spring positioned around a portion of said elongated body.

5. The sensor of claim 4 wherein said elongated body carries three substantially parallel axial channels in the upper portion thereof, each of said channels containing a conductive strip, one of said conductive strips being the electric lead which is contacted with said inner contact portion and the other conductive strips being said contact leads of said heater element means.

6. The sensor of claim 1 wherein said electric resistor heater element means comprises twin resistance wires double wound around the said insulator body, one end of each of said resistance wires joining a respective contact lead, the other end of said wires being joined to complete the heater circuit.

7. The sensor of claim 6 wherein said electric lead which is in contact with said inner contact portion is located parallel to said resistance wires along at least a portion of the length of said elongated insulator body.

8. The sensor according to each of claims 1-7 wherein said electric lead which is in contact with said inner contact portion and the said resistance wires or the contact leads joined thereto are located for at least a portion of their respective length in channels or grooves in the body of said elongated insulator.

9. The sensor of claim 1 wherein an electrically conductive contact plate as contact portion is positioned at the bottom of said elongated insulator body in resilient contact with the inside portion of the closed end of said tubular solid electrolyte.

10. The sensor of claim 9 wherein said electrically conductive plate is shaped to substantially conform to the inside surface of the closed end of said tubular solid electrolyte.

11. The sensor of claim 1 wherein (i) said electric lead which is in contact with said inner contact portion and (ii) each of said contact leads of said heater element means is in the form of an electric strip on a surface of said elongated insulator body.

12. The sensor of claim 11 wherein said electric lead and said contact leads are in the form of conductive strips which at the end of the sensor away from that which is adapted to be exposed to the exhaust gas, terminate in the three respective terminals for the sensor.

13. The sensor of claim 1 wherein said inner elongated insulator body is a central tubular or rod body carrying within it (i) said electric lead which is in contact with said inner contact portion and (ii) each of said contact leads of said heater element means.

* * * * *